(12) United States Patent
Yamagata et al.

(10) Patent No.: US 7,354,949 B2
(45) Date of Patent: *Apr. 8, 2008

(54) THERAPEUTIC AGENT FOR BLADDER IRRITATIVE SYMPTOMS ASSOCIATED WITH BENIGN PROSTATIC HYPERPLASIA

(75) Inventors: Tsuyoshi Yamagata, Sunto-gun (JP); Kaoru Atsuki, Sunto-gun (JP); Tetsuji Ohno, Sunto-gun (JP); Shiro Shirakura, Mishima (JP); Akira Karasawa, Sunto-gun (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/472,148

(22) PCT Filed: Mar. 29, 2002

(86) PCT No.: PCT/JP02/03169

§ 371 (c)(1),
(2), (4) Date: Sep. 22, 2003

(87) PCT Pub. No.: WO02/078712

PCT Pub. Date: Oct. 10, 2002

(65) Prior Publication Data

US 2004/0110784 A1    Jun. 10, 2004

(30) Foreign Application Priority Data

Mar. 30, 2001 (JP) ............................. 2001-099799

(51) Int. Cl.
     *A61K 31/38*      (2006.01)
     *A61K 31/44*      (2006.01)
     *A61K 31/42*      (2006.01)

(52) U.S. Cl. ....................... 514/431; 514/291; 514/375

(58) Field of Classification Search ................ 514/431, 514/291, 375

See application file for complete search history.

(56) References Cited

U.S. PATENT DOCUMENTS 5,726,325 A    3/1998   Yoshida et al. ................ 549/48
6,211,227 B1    4/2001   Yoshida et al. ............. 514/431

FOREIGN PATENT DOCUMENTS

WO        97/14672      4/1997
WO        98/46587     10/1998

OTHER PUBLICATIONS

Yoshimura, et al., "Increased Excitability of Afferent Neurons Innervating Rat Urinary Bladd r after Chronic Bladder Inflammation", *The Journal of Neuroscience*, (1999), vol. 19, No. 11, pp. 4644-4653.
Yoshimura, Bladder Afferent Pathway and Spinal Cord Injury: Possible Mechanisms Inducing Hyperreflexcia of the Urinary Bladder, *Progress in Neurobiology*, vol. 57, (1999), pp. 583-606.
Buttyan, et al., "Animal Models of Bladder Outlet Obstruction and Molecular Insights into the Basis for the Development of Bladder Dysfunction", Eur Urol, vol. 32, Supp 1 (1997), p. 32-39.
Valesco, et al."Effects of intravenous and infravesical administration of suramin, terazosin and BMY 7378 on bladder instability in conscious rats with bladder outlet obstruction", BJU International, vol. 92 (2003), p. 131-136.

*Primary Examiner*—Raymond J. Henley, III
(74) *Attorney, Agent, or Firm*—Fitzpatrick, Cella, Harper & Scinto

(57) ABSTRACT

The present invention provides a therapeutic agent for bladder irritative symptoms associated with benign prostatic hyperplasia comprising, as an active ingredient, a tricyclic compound represented by formula (I):

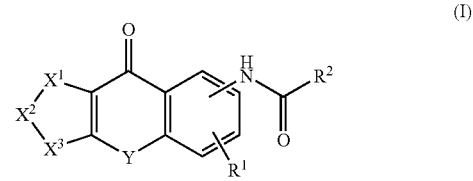

[wherein $R^1$ represents a hydrogen atom, substituted or unsubstituted lower alkyl, substituted or unsubstituted lower alkoxy or halogen;
$X^1$-$X^2$-$X^3$ represents $CR^5$=$CR^6$—$CR^7$=$CR^8$, $N(O)_m$=$CR^6$—$CR^7$=$CR^8$, $CR^5$=$CR^6$—$N(O)_m$=$CR^8$, $CR^5$=$CR^6$—$CR^7$=$N(O)_m$, $CR^5$=$CR^6$—O, $CR^5$=$CR^6$—S, O—$CR^7$=$CR^8$, S—$CR^7$=$CR^8$ or O—$CR^7$=N;
Y represents 13 $CH_2S$—, —$CH_2SO$—, —$CH_2SO_2$—, —$CH_2O$—, —CH=CH—, —$(CH_2)_p$—, —$SCH_2$—, —$SOCH_2$—, —$SO_2CH_2$— or —$OCH_2$—; and
$R^2$ represents a hydrogen atom, substituted or unsubstituted lower alkyl, substituted or unsubstituted lower alkenyl, substituted or unsubstituted lower alkoxy, amino, mono (substituted or unsubstituted lower alkyl)-substituted amino, di(substituted or unsubstituted lower alkyl)-substituted amino, substituted or unsubstituted aryl, substituted or unsubstituted heteroaryl, substituted or unsubstituted aralkylamino, substituted or unsubstituted arylamino or a substituted or unsubstituted heteroalicyclic group] or a pharmaceutically acceptable salt thereof.

3 Claims, No Drawings

THERAPEUTIC AGENT FOR BLADDER IRRITATIVE SYMPTOMS ASSOCIATED WITH BENIGN PROSTATIC HYPERPLASIA

TECHNICAL FIELD

The present invention relates to a therapeutic agent for bladder irritative symptoms associated with benign prostatic hyperplasia.

BACKGROUND ART

Benign prostatic hyperplasia is benign adenoma generated in a transitional zone of the prostate that wraps the urethra. Patients with benign prostatic hyperplasia complain of bladder outlet obstructive symptoms or bladder irritative symptoms. Examples of bladder outlet obstructive symptoms include a hesitation before urine flow starts, straining, a weak urinary stream, an intermittent urinary stream, dribbling at the end of urination, prolongation of urination and overflow incontinence. Examples of bladder irritative symptoms include urinary frequency at daytime, urinary frequency at night, urinary urgency, a feeling of incomplete emptying and a reduced voided volume per micturition. Functional obstruction and mechanical obstruction are involved in the development of these urinary disturbances due to benign prostatic hyperplasia. Further, these functional and mechanical obstructions cause secondary changes in detrusor muscle or nerves, which induce the complicated pathological phenomena such as bladder irritative symptoms and bladder outlet obstructive symptoms.

At present, for examples, $\alpha_1$-receptor blockers, anti-androgen agents, plant preparations, amino acid preparations, or the like are used as a therapeutic agent for benign prostatic hyperplasia. Among these, examples of the $\alpha_1$-receptor blockers include tamsulosin hydrochloride, prazosin hydrochloride, terazosin hydrochloride and urapidil. Examples of the anti-androgen agents include chlormadinone acetate, allylestrenol, gestonorone caproate, oxendolone and finasteride. The $\alpha_1$-receptor blockers inhibit the functional urethral obstruction, that is, contractions of prostatic smooth muscle induced by noradrenaline, secreted by stimulation of the sympathetic nerve, via the $\alpha_1$-receptor. The anti-androgen agents inhibit the mechanical obstruction, that is, a rise in urethral resistance resulting from the pressure caused by the enlarged prostate itself. However, although the $\alpha_1$-receptor blockers and anti-androgen agents are recognized to be effective for bladder outlet obstructive symptoms of benign prostatic hyperplasia, their effects on improvement of bladder irritative symptoms are insufficient. The plant preparations and amino acid preparations, which have anti-inflammatory activity, anti-edema activity, or the like, improve the bladder irritative symptoms by alleviating the outflow obstruction at the bladder neck; but their effects are weak and the dose required is large so that they are a burden to aged people. Under these circumstances, there exists a need for a therapeutic agent to alleviate bladder irritative symptoms.

Tricyclic compounds having the activity to prolong the intervals of bladder contractions and pharmaceutically acceptable salts thereof are known as therapeutic agents for urinary incontinence (WO97/14672 and WO98/46587). However, it is not known that the compound groups have the activity to remit bladder irritative symptoms associated with benign prostatic hyperplasia.

DISCLOSURE OF THE INVENTION

The present invention relates to the following (1) to (27).
(1) A therapeutic agent for bladder irritative symptoms associated with benign prostatic hyperplasia comprising, as an active ingredient, a tricyclic compound represented by formula (I):

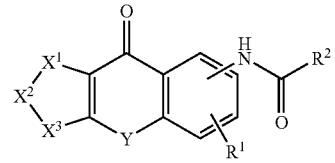

(I)

[wherein $R^1$ represents a hydrogen atom, substituted or unsubstituted lower alkyl, substituted or unsubstituted lower alkoxy or halogen;
$X^1$-$X^2$-$X^3$ represents $CR^5$=$CR^6$—$CR^7$=$CR^8$ (wherein $R^5$, $R^6$, $R^7$ and $R^8$, which may be the same or different, each represent a hydrogen atom, substituted or unsubstituted lower alkyl, hydroxy, substituted or unsubstituted lower alkoxy, nitro, amino, mono(lower alkyl)-substituted amino, di(lower alkyl)-substituted amino, substituted or unsubstituted lower alkanoylamino or halogen), $N(O)^m$=$CR^6$—$CR^7$=$CR^8$ (wherein $R^6$, $R^7$ and $R^8$ have the same significances as defined above, respectively, and m represents 0 or 1), $CR^5$=$CR^6$—$N(O)_m$=$CR^8$ (wherein $R^5$, $R^6$, $R^8$ and m have the same significances as defined above, respectively), $CR^5$=$CR^6$—$CR^7$=$N(O)_m$ (wherein $R^5$, $R^6$, $R^7$ and m have the same significances as defined above, respectively), $CR^5$=$CR^6$—O (wherein $R^5$ and $R^6$ have the same significances as defined above, respectively), $CR^5$=$CR^6$—S (wherein $R^5$ and $R^6$ have the same significances as defined above, respectively), O—$CR^7$=$CR^8$ (wherein $R^7$ and $R^8$ have the same significances as defined above, respectively), S—$CR^7$=$CR^8$ (wherein $R^7$ and $R^8$ have the same significances as defined above, respectively) or O—$CR^7$=N (wherein $R^7$ has the same significance as defined above);
Y represents —$CH_2S$—, —$CH_2SO$—, —$CH_2SO_2$—, —$CH_2O$—, —CH=CH—, —$(CH_2)_p$— (wherein p represents an integer of 0 to 2), —$SCH_2$—, —$SOCH_2$—, —$SO_2CH_2$— or —$OCH_2$—; and
$R^2$ represents a hydrogen atom, substituted or unsubstituted lower alkyl, substituted or unsubstituted lower alkenyl, substituted or unsubstituted lower alkoxy, amino, mono(substituted or unsubstituted lower alkyl)-substituted amino, di(substituted or unsubstituted lower alkyl)-substituted amino, substituted or unsubstituted aryl, substituted or unsubstituted heteroaryl, substituted or unsubstituted aralkylamino, substituted or unsubstituted arylamino or a substituted or unsubstituted heteroalicyclic group] or a pharmaceutically acceptable salt thereof.
(2) A therapeutic agent for bladder irritative symptoms associated with benign prostatic hyperplasia comprising, as an active ingredient, a tricyclic compound represented by formula (Ia):

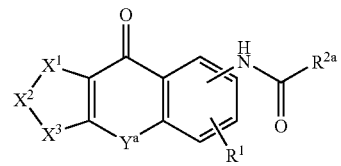

(Ia)

[wherein $R^1$ and $X^1$-$X^2$-$X^3$ have the same significances as defined above, respectively;

$Y^a$ represents —$CH_2SO_2$—, —$SCH_2$—, —$SOCH_2$—, —$SO_2CH_2$— or —$OCH_2$—; and when $Y^a$ is —$CH_2SO_2$—, —$SCH_2$—, —$SOCH_2$— or —$SO_2CH_2$—, $R^{2a}$ represents a hydrogen atom, substituted or unsubstituted lower alkyl, substituted or unsubstituted lower alkenyl, trifluoromethyl, substituted or unsubstituted lower alkoxy, amino, mono(substituted or unsubstituted lower alkyl)-substituted amino, di(substituted or unsubstituted lower alkyl)-substituted amino, substituted or unsubstituted aryl, substituted or unsubstituted heteroaryl, substituted or unsubstituted aralkylamino, substituted or unsubstituted arylamino, a substituted or unsubstituted heteroalicyclic group or formula (II):

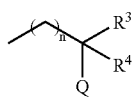

(wherein n is 0 or 1; $R^3$ and $R^4$, which may be the same or different, each represent a hydrogen atom, substituted or unsubstituted lower alkyl, substituted or unsubstituted cycloalkyl, substituted or unsubstituted aryl, substituted or unsubstituted aralkyl or trifluoromethyl, or $R^3$ and $R^4$ may be combined together with the adjacent carbon atom to form cycloalkyl; and Q represents hydroxy, substituted or unsubstituted lower alkoxy, amino or halogen), and when $Y^a$ is —$OCH_2$—, $R^{2a}$ represents a hydrogen atom, substituted or unsubstituted lower alkenyl, trifluoromethyl, substituted or unsubstituted lower alkoxy, amino, mono(substituted or unsubstituted lower alkyl)-substituted amino, di(substituted or unsubstituted lower alkyl)-substituted amino, substituted or unsubstituted aryl, substituted or unsubstituted heteroaryl, substituted or unsubstituted aralkylamino, substituted or unsubstituted arylamino, a substituted or unsubstituted heteroalicyclic group or formula (II):

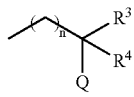

(wherein n, $R^3$, $R^4$ and Q have the same significances as defined above, respectively)] or a pharmaceutically acceptable salt thereof.

(3) The therapeutic agent for bladder irritative symptoms associated with benign prostatic hyperplasia comprising, as an active ingredient, a tricyclic compound or a pharmaceutically acceptable salt thereof according to (2), wherein $Y^a$ is —$CH_2SO_2$—, —$SCH_2$—, —$SOCH_2$— or —$SO_2CH_2$—.

(4) The therapeutic agent for bladder irritative symptoms associated with benign prostatic hyperplasia comprising, as an active ingredient, a tricyclic compound or a pharmaceutically acceptable salt thereof according to (2), wherein $Y^a$ is —$OCH_2$—.

(5) The therapeutic agent for bladder irritative symptoms associated with benign prostatic hyperplasia comprising, as an active ingredient, a tricyclic compound or a pharmaceutically acceptable salt thereof according to any of (2) to (4), wherein $R^1$ is a hydrogen atom, substituted or unsubstituted lower alkoxy or halogen.

(6) The therapeutic agent for bladder irritative symptoms associated with benign prostatic hyperplasia comprising, as an active ingredient, a tricyclic compound or a pharmaceutically acceptable salt thereof according to any of (2) to (4), wherein $R^1$ is a hydrogen atom.

(7) The therapeutic agent for bladder irritative symptoms associated with benign prostatic hyperplasia comprising, as an active ingredient, a tricyclic compound or a pharmaceutically acceptable salt thereof according to any of (2), (5) and (6), wherein $Y^a$ is —$CH_2SO_2$—, —$SO_2CH_2$— or —$OCH_2$—.

(8) The therapeutic agent for bladder irritative symptoms associated with benign prostatic hyperplasia comprising, as an active ingredient, a tricyclic compound or a pharmaceutically acceptable salt thereof according to any of (2), (5) and (6), wherein $Y^a$ is —$CH_2SO_2$— or —$SO_2CH_2$—.

(9) The therapeutic agent for bladder irritative symptoms associated with benign prostatic hyperplasia comprising, as an active ingredient, a tricyclic compound or a pharmaceutically acceptable salt thereof according to any of (2), (5) and (6), wherein $Y^a$ is —$CH_2SO_2$—.

(10) The therapeutic agent for bladder irritative symptoms associated with benign prostatic hyperplasia comprising, as an active ingredient, a tricyclic compound or a pharmaceutically acceptable salt thereof according to any of (2) to (9), wherein $X^1$-$X^2$-$X^3$ is S—$CR^7$=$CR^8$ (wherein $R^7$ and $R^8$ have the same significances as defined above, respectively).

(11) The therapeutic agent for bladder irritative symptoms associated with benign prostatic hyperplasia comprising, as an active ingredient, a tricyclic compound or a pharmaceutically acceptable salt thereof according to any of (2) to (9), wherein $X^1$-$X^2$-$X^3$ is $CR^5$=$CR^6$—$CR^7$=$CR^8$ (wherein $R^5$, $R^6$, $R^7$ and $R^8$ have the same significances as defined above, respectively).

(12) The therapeutic agent for bladder irritative symptoms associated with benign prostatic hyperplasia comprising, as an active ingredient, a tricyclic compound or a pharmaceutically acceptable salt thereof according to any of (2) to (11), wherein $R^{2a}$ is formula (II):

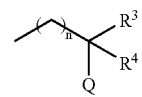

(wherein n, $R^3$, $R^4$ and Q have the same significances as defined above, respectively).

(13) The therapeutic agent for bladder irritative symptoms associated with benign prostatic hyperplasia comprising, as an active ingredient, a tricyclic compound or a pharmaceutically acceptable salt thereof according to (12), wherein n is 0.

(14) The therapeutic agent for bladder irritative symptoms associated with benign prostatic hyperplasia comprising, as an active ingredient, a tricyclic compound or a pharmaceutically acceptable salt thereof according to (13), wherein $R^3$ is methyl, $R^4$ is trifluoromethyl, and Q is hydroxy.

(15) The therapeutic agent for bladder irritative symptoms associated with benign prostatic hyperplasia comprising, as an active ingredient, a tricyclic compound or a pharmaceutically acceptable salt thereof according to (2), wherein $R^1$ is a hydrogen atom, $Y^a$ is —$CH_2SO_2$—, $X^1$-$X^2$-$X^3$ is S—$CR^7$=$CR^8$ (wherein $R^7$ and $R^8$ have the same significances as defined above, respectively), and $R^2$ is formula (III):

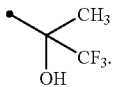

(16) A therapeutic agent for bladder irritative symptoms associated with benign prostatic hyperplasia comprising, as an active ingredient, a tricyclic compound represented by formula (Ib):

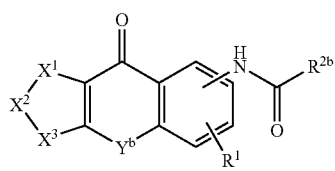

[wherein $R^1$ and $X^1$-$X^2$-$X^3$ have the same significances as defined above, respectively;
$Y^b$ represents —$CH_2O$—, —$CH_2S$—, —$CH_2SO$—, —CH=CH— or —$(CH_2)_p$— (wherein p has the same significance as defined above); and $R^{2b}$ represents formula (III):

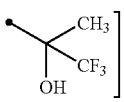

or a pharmaceutically acceptable salt thereof.

(17) The therapeutic agent for bladder irritative symptoms associated with benign prostatic hyperplasia comprising, as an active ingredient, a tricyclic compound or a pharmaceutically acceptable salt thereof according to (16), wherein $X^1$-$X^2$-$X^3$ is $CR^5$=$CR^6$—$CR^7$=$CR^8$ (wherein $R^5$, $R^6$, $R^7$ and $R^8$ have the same significances as defined above, respectively) or $CR^5$=$CR^6$—$CR^7$=N (wherein $R^5$, $R^6$ and $R^7$ have the same significances as defined above, respectively).

(18) The therapeutic agent for bladder irritative symptoms associated with benign prostatic hyperplasia comprising, as an active ingredient, a tricyclic compound or a pharmaceutically acceptable salt thereof according to (16), wherein $X^1$-$X^2$-$X^3$ is $CR^5$=$CR^6$—O (wherein $R^5$ and $R^6$ have the same significances as defined above, respectively) or $CR^5$=$CR^6$—S (wherein $R^5$ and $R^6$ have the same significances as defined above, respectively).

(19) The therapeutic agent for bladder irritative symptoms associated with benign prostatic hyperplasia comprising, as an active ingredient, a tricyclic compound or a pharmaceutically acceptable salt thereof according to (16), wherein $X^1$-$X^2$-$X^3$ is O—$CR^7$=$CR^8$ (wherein $R^7$ and $R^8$ have the same significances as defined above, respectively) or S—$CR^7$=$CR^8$ (wherein $R^7$ and $R^8$ have the same significances as defined above, respectively).

(20) The therapeutic agent for bladder irritative symptoms associated with benign prostatic hyperplasia comprising, as an active ingredient, a tricyclic compound or a pharmaceutically acceptable salt thereof according to any of (16) to (19), wherein $Y^b$ is —$CH_2O$—.

(21) The therapeutic agent for bladder irritative symptoms associated with benign prostatic hyperplasia comprising, as an active ingredient, a tricyclic compound or a pharmaceutically acceptable salt thereof according to any of (16) to (19), wherein $Y^b$ is —$(CH_2)_p$— (wherein p has the same significance as defined above).

(22) The therapeutic agent for bladder irritative symptoms associated with benign prostatic hyperplasia comprising, as an active ingredient, a tricyclic compound or a pharmaceutically acceptable salt thereof according to (21), wherein p is 0.

(23) The therapeutic agent for bladder irritative symptoms associated with benign prostatic hyperplasia comprising, as an active ingredient, a tricyclic compound or a pharmaceutically acceptable salt thereof according to (21), wherein p is 2.

(24) The therapeutic agent for bladder irritative symptoms associated with benign prostatic hyperplasia comprising, as an active ingredient, a tricyclic compound or a pharmaceutically acceptable salt thereof according to any of (16) to (19), wherein $Y^b$ is —CH=CH—.

(25) The therapeutic agent for bladder irritative symptoms associated with benign prostatic hyperplasia comprising, as an active ingredient, a tricyclic compound or a pharmaceutically acceptable salt thereof according to any of (16) to (19), wherein $Y^b$ is —$CH_2S$— or —$CH_2SO$—.

(26) Use of the tricyclic compound or the pharmaceutically acceptable salt thereof according to any of (1) to (25) for the production of a therapeutic agent for bladder irritative symptoms associated with benign prostatic hyperplasia.

(27) A method for treating bladder irritative symptoms associated with benign prostatic hyperplasia, comprising a step of administering an effective amount of the tricyclic compound or the pharmaceutically acceptable salt thereof according to any of (1) to (25).

Hereinafter, the compounds represented by formula (I) are referred to as Compounds (I), and the same applies to the compounds of other formula numbers.

In the definitions of the groups in formula (I), the lower alkyl moiety of the lower alkyl, the lower alkoxy, the mono(lower alkyl)-substituted amino and the di(lower alkyl)-substituted amino includes straight-chain or branched lower alkyl groups having 1 to 8 carbon atoms, such as methyl, ethyl, propyl, isopropyl, butyl, isobutyl, sec-butyl, tert-butyl, pentyl, hexyl, 1,2,2-trimethylpropyl, heptyl and octyl. The two lower alkyl moieties of the di(lower alkyl)-substituted amino may be the same or different.

The lower alkanoyl moiety of the lower alkanoylamino includes lower alkanoyl groups having 1 to 6 carbon atoms, such as formyl, acetyl, propanoyl, butanoyl, pentanoyl, 2,2-dimethylpropanoyl and hexanoyl.

The lower alkenyl includes straight-chain or branched lower alkenyl groups having 2 to 6 carbon atoms, such as vinyl, allyl, 1-propenyl, methacryl, 1-butenyl, crotyl, pentenyl and hexenyl.

The aryl and the aryl moiety of the arylamino include aryl groups having 6 to 14 carbon atoms, such as phenyl, naphthyl and anthranyl.

The heteroaryl includes 5- or 6-membered monocyclic heteroaromatic groups containing at least one atom selected from the group consisting of a nitrogen atom, an oxygen atom and a sulfur atom, and bicyclic or tricyclic condensed heteroaromatic groups in which 3- to 8-membered rings are condensed and which contain at least one atom selected from the group consisting of a nitrogen atom, an oxygen atom and a sulfur atom. Specific examples are pyridyl, furyl, thienyl, quinolyl, imidazolyl, benzimidazolyl, thiazolyl, pyrazinyl, pyrimidinyl, pyridazinyl, isoquinolinyl, phthalazinyl, quinazolinyl, quinoxalinyl, naphthyridinyl, cinnolinyl, pyrrolyl, pyrazolyl, triazolyl, tetrazolyl, oxazolyl, indolyl, benzotriazolyl, benzothiazolyl, benzoxazolyl, purinyl, and the like.

The aralkyl moiety of the aralkylamino includes aralkyl groups having 7 to 12 carbon atoms, such as benzyl, phenethyl and naphthylmethyl.

The heteroalicyclic group includes 3- to 8-membered monocyclic heteroalicyclic groups containing at least one atom selected from the group consisting of a nitrogen atom, an oxygen atom and a sulfur atom, and bicyclic or tricyclic condensed heteroalicyclic groups in which 3- to 8-membered rings are condensed and which contain at least one atom selected from the group consisting of a nitrogen atom, an oxygen atom and a sulfur atom. Specific examples are tetrahydropyridinyl, tetrahydroquinolinyl, tetrahydroisoquinolinyl, tetrahydropyranyl, tetrahydrofuranyl, dihydrobenzofuranyl, pyrrolidinyl, piperidino, piperidinyl, perhydroazepinyl, perhydroazocinyl, morpholino, morpholinyl, thiomorpholino, thiomorpholinyl, piperazinyl, homopiperidino, homopiperazinyl, dioxolanyl, imidazolidinyl, imidazolinyl, pyrazolidinyl, indolinyl, isoindolinyl, pyrrolinyl, pyrrolidonyl, piperidonyl, perhydroazepinonyl, thiazolidonyl, oxazolidonyl, succinimido, phthalimido, glutarimido, maleimido, hydantoinyl, thiazolidinedionyl, oxazolidinedionyl, tetrahydrothienyl, chromanyl, pipecolinyl, and the like.

The halogen means a fluorine, chlorine, bromine or iodine atom.

The substituted lower alkyl, the substituted lower alkoxy, the mono(substituted lower alkyl)-substituted amino, the di(substituted lower alkyl)-substituted amino, the substituted lower alkanoylamino and the substituted lower alkenyl each have 1 to a substitutable number (preferably 1 to 6, more preferably 1 to 4) of substituents which are the same or different. Examples of the substituents are hydroxy, halogen, nitro, amino, carboxy, mono(lower alkyl)-substituted amino, di(lower alkyl)-substituted amino, lower alkoxy, cycloalkyl, substituted cycloalkyl [the substituted cycloalkyl has 1 to 3 substituents which are the same or different, such as hydroxy, halogen, nitro, amino, mono (lower alkyl)-substituted amino, di(lower alkyl)-substituted amino or lower alkoxy], aryl, substituted aryl (the substituent in the substituted aryl has the same significance as that in the substituted aryl described below), aralkyl, substituted aralkyl (the substituent in the substituted aralkyl has the same significance as that in the substituted aralkyl described below), substituted lower alkoxy [the substituted lower alkoxy has 1 to 3 substituents which are the same or different, such as hydroxy, halogen, nitro, amino, mono (lower alkyl)-substituted amino, di(lower alkyl)-substituted amino or lower alkoxy], and the like. In the above, the cycloalkyl may be bound to the substituted lower alkyl by spiro-union. Herein, the halogen has the same significance as defined above, the lower alkyl moiety of the mono(lower alkyl)-substituted amino, the di(lower alkyl)-substituted amino and the lower alkoxy has the same significance as the above-described lower alkyl, and the aryl has the same significance as defined above. The cycloalkyl includes cycloalkyl groups having 3 to 8 carbon atoms, such as cyclopropyl, cyclobutyl, cyclopentyl, cyclohexyl, cycloheptyl and cyclooctyl. The aralkyl includes aralkyl groups having 7 to 12 carbon atoms, such as benzyl, phenethyl and naphthylmethyl.

The substituted aryl, the substituted heteroaryl, the substituted aralkylamino and the substituted arylamino each have 1 to 3 substituents which are the same or different. Examples of the substituents are lower alkyl, hydroxy, amino, halogen, and the like, and the lower alkyl and the halogen have the same significances as defined above, respectively.

The substituted heteroalicyclic group has 1 to 3 substituents which are the same or different. Examples of the substituents are lower alkyl, hydroxy, halogen, and the like, and the lower alkyl and the halogen have the same significances as defined above, respectively.

In the definitions of formula (Ia) and formula (Ib), the lower alkyl moiety of the lower alkyl, the lower alkoxy, the mono(lower alkyl)-substituted amino and the di(lower alkyl)-substituted amino includes straight-chain or branched lower alkyl groups having 1 to 6 carbon atoms, such as methyl, ethyl, propyl, isopropyl, butyl, isobutyl, sec-butyl, tert-butyl, pentyl, hexyl and 1,2,2-trimethylpropyl. The two lower alkyl moieties of the di(lower alkyl)-substituted amino may be the same or different.

The halogen, the lower alkenyl, the aryl moiety of the aryl and the arylamino, the heteroaryl, the aralkyl moiety of the aralkyl and the aralkylamino, the heteroalicyclic group and the cycloalkyl respectively have the same significances as the halogen, the lower alkenyl, the aryl, the heteroaryl, the aralkyl, the heteroalicyclic group and the cycloalkyl in the definitions of the groups in formula (I) or in the definitions of the substituents in the definitions of the groups in formula (I).

The substituted lower alkyl, the substituted lower alkoxy, the mono(substituted lower alkyl)-substituted amino, the di(substituted lower alkyl)-substituted amino, the substituted lower alkenyl and the substituted cycloalkyl each have 1 to 3 substituents which are the same or different. Examples of the substituents are hydroxy, halogen, nitro, amino, carboxy, mono(lower alkyl)-substituted amino, di(lower alkyl)-substituted amino, lower alkoxy, and the like. The halogen has the same significance as defined above, and the lower alkyl moiety of the mono(lower alkyl)-substituted amino, the di(lower alkyl)-substituted amino and the lower alkoxy has the same significance as the above-described lower alkyl.

The substituted aryl, the substituted heteroaryl, the substituted aralkyl, the substituted aralkylamino and the substituted arylamino each have 1 to 3 substituents which are the same or different. Examples of the substituents are lower alkyl, hydroxy, amino, halogen, and the like, and the lower alkyl and the halogen have the same significances as defined above, respectively.

The substituted heteroalicyclic group has 1 to 3 substituents which are the same or different. Examples of the substituents are lower alkyl, hydroxy, halogen, and the like, and the lower alkyl and the halogen have the same significances as defined above, respectively.

The pharmaceutically acceptable salts of Compound (I), Compound (Ia) and Compound (Ib) include pharmaceutically acceptable acid addition salts, metal salts, ammonium salts, organic amine addition salts and amino acid addition salts. Examples of the acid addition salts are inorganic acid addition salts such as hydrochloride, hydrobromide, hydroiodide, nitrate, sulfate and phosphate, and organic acid addition salts such as formate, acetate, benzoate, maleate, fumarate, succinate, tartrate, citrate, oxalate, glyoxylate, methanesulfonate, ethanesulfonate, benzenesulfonate and lactate. Examples of the metal salts are alkali metal salts such as a lithium salt, a sodium salt and a potassium salt, alkaline earth metal salts such as a magnesium salt and a calcium salt, an aluminum salt, a zinc salt, and the like. Examples of the ammonium salts are ammonium, tetramethylammonium, and the like. Examples of the organic amine addition salts are salts with morpholine, piperidine, or the like, and examples of the amino acid addition salts are salts with glycine, phenylalanine, aspartic acid, glutamic acid, lysine, or the like.

The tricyclic compounds used in the present invention can be produced according to the methods disclosed in the above publications or similar methods, and can be isolated and purified by purification methods conventionally used in synthetic organic chemistry, for example, neutralization, filtration, extraction, washing, drying, concentration, recrystallization and various kinds of chromatography.

When it is desired to obtain a salt of the tricyclic compound used in the present invention, in the case where it is produced in the form of the salt, it can be subjected to purification as such, and where it is produced in the form of a free base, it can be converted into a salt, after being dissolved or suspended in a suitable solvent, by adding an acid or a base thereto.

There may be optical isomers for some of the tricyclic compounds used in the present invention. All possible stereoisomers and mixtures thereof can be used as active ingredients of the therapeutic agent of the present invention.

The tricyclic compounds or pharmaceutically acceptable salts thereof used in the present invention may exist in the form of adducts with water or various solvents, which can also be used as active ingredients of the therapeutic agent of the present invention.

The pharmacological activities of typical Compound (I) are described in test examples. In Test Examples 1-3, (S)-(+)-N-(5,5-dioxido-10-oxo-4,10-dihydrothieno[3,2-c][1]benzothiepin-9-yl)-3,3,3-trifluoro-2-hydroxy-2-methyl-propanamide was used as a test compound. Hereinafter, the above compound is referred to as Compound 1. Compound 1 is the same compound as Compound (1-25) described in WO98/46587.

The pharmacological activities of Compound (I) are described in the following test examples.

TEST EXAMPLE 1

Inhibitory Activity on Urinary Frequency Due to Partial Urethral Obstruction

The experiment was carried out according to the method of Saito, et al. [J. Urol., Vol. 150, pp. 1045-1051 (1993)].

Male SD rats of 8 to 9 weeks of age (supplied by Japan SLC) were used in the test. Five to seven animals of these rats were put in each metal cage and reared by allowing them to freely take commercially available chow and water, in an animal room at room temperature between 19 and 25° C. and humidity between 30 and 70% under illumination for 12 hours (from 7:00 a.m. to 7:00 p.m.) per day.

The rats were subjected to operation of partial urethral obstruction. Each rat was anesthetized by intraperitoneal administration of 50 mg/kg pentobarbital sodium (Dainippon Pharmaceutical Co., Ltd.) and placed in the supine position. The abdominal midline incision was made in a length of about 1 cm to expose the bladder, prostate and the urethra. After the bladder neck and base were peeled from the prostate, two surgical suture threads (No. 3, Natsume Seisakusho Co., Ltd.) were passed behind the urethral base. A polyethylene tube (PE-200, Nippon Becton Dickinson Co., Ltd.) was placed along the urethra, and the urethra was loosely double-ligated together with the tube. The ligation was made in such a manner that the urethra was not pressed with the polyethylene tube and the suture was not slack. Then, the polyethylene tube was pulled out and the urethra was partially obstructed. The incised part of abdomen was sutured with a surgical thread.

Five to seven days after the partial urethral obstruction operation, the rats with partial urethral obstruction and the sham-operated rats were put in metabolic cages (KN-649, Natsume Seisakusho Co., Ltd.). For acclimation, the rats were reared for one day with free drinking and feeding, and the micturition test was started the following day. The amount of urination in the rats was continuously measured as the weight using an electronic balance (HF-200, A & D Company Ltd.), and was recorded on a thermal array recorder (RTA-1200, Nihon Kohden Corp.) via a direct current amplifier (AD-601G, Nihon Kohden Corp.). The data were collected during the light period under illumination (9:00-18:00) and the dark period without illumination (19:00-4:00), and the number of micturitions and the micturition volume in each period were measured to calculate the urinary frequency (the number of micturitions per 9 hours), the voided volume per micturition and the total urine volume as the measurement parameters. The voided volume per micturition was calculated by dividing the total urine volume per 9 hours by the urinary frequency per 9 hours. On the next day, a test compound or a vehicle (0.5 w/v% aqueous methylcellulose 400 cP solution) was orally administered twice (between 8:00 and 9:00, and between 18:00 and 19:00). The number of micturitions and the urine volume were measured from 9:00 to 18:00 and from 19:00 to 4:00 in the same manner as on the previous day to obtain the measurement values. The changes in the values of each parameter induced by the administration of the compound were also calculated. In the sham-operated group, the urinary frequency, the voided volume per micturition and the total urine volume obtained on the first day of the micturition test were compared with those in the groups of partial urethral obstruction. The average±standard error of the urinary frequency, voided volume per micturition and the total urine volume was calculated for each group.

The results are shown as follows: Table 1, urinary frequency; Table 2, voided volume per micturition; and Table 3, total urine volume.

TABLE 1

| | Urinary frequency (micturitions/9 hours) | |
|---|---|---|
| | Before administration | After administration |
| Light period (Inactive period) | | |
| Sham-operated group | 4.3 ± 0.6 | 5.2 ± 0.7 |
| Control group | 8.9 ± 1.0 | 9.0 ± 0.7 |
| Compound 1 | 8.7 ± 0.8 | 5.3 ± 0.4*** |
| Dark period (Active period) | | |
| Sham-operated group | 7.3 ± 0.8 | 7.2 ± 1.1 |
| Control group | 8.6 ± 0.6 | 10.3 ± 1.0 |
| Compound 1 | 10.0 ± 1.3 | 6.7 ± 1.2* |

*p < 0.05,
***p < 0.001 (comparison with the control group) (n = 6-7; Student's t-test)

TABLE 2

| | Voided volume per micturition (mL) | |
|---|---|---|
| | Before administration | After administration |
| Light period (Inactive period) | | |
| Sham-operated group | 1.058 ± 0.154 | 0.947 ± 0.149 |
| Control group | 0.678 ± 0.102 | 0.584 ± 0.090 |
| Compound 1 | 0.577 ± 0.064 | 0.899 ± 0.127 |
| Dark period (Active period) | | |
| Sham-operated group | 0.507 ± 0.093 | 0.630 ± 0.086 |
| Control group | 0.493 ± 0.047 | 0.475 ± 0.059 |
| Compound 1 | 0.362 ± 0.038 | 0.771 ± 0.160 |

TABLE 3

| | Total urine volume (mL/9 hours) | |
|---|---|---|
| | Before administration | After administration |
| Light period (Inactive period) | | |
| Sham-operated group | 4.29 ± 0.47 | 4.47 ± 0.50 |
| Control group | 5.68 ± 0.87 | 5.19 ± 0.86 |
| Compound 1 | 4.80 ± 0.31 | 4.76 ± 0.78 |
| Dark period (Active period) | | |
| Sham-operated group | 3.48 ± 0.47 | 4.27 ± 0.74 |
| Control group | 4.29 ± 0.64 | 4.89 ± 0.69 |
| Compound 1 | 3.57 ± 0.57 | 4.83 ± 0.83 |

In Test Example 1, Compound 1 significantly decreased the urinary frequency and tended to increase the voided volume per micturition. From the result, Compound 1 is considered to be useful as a therapeutic agent for increased urinary frequency accompanied by benign prostatic hyperplasia.

TEST EXAMPLE 2

Activity to Increase the Bladder Capacity of Rats with Partial Urethral Obstruction The experiment was carried out according to the method of Saito, et al. [J. Urol., Vol. 150, pp. 1045-1051 (1993)].

Male SD rats of 8 to 9 weeks of age (supplied by Japan SLC) were used in the test. Five to seven rats were put in each metal cage and reared by allowing them to freely take commercially available chow and water, in an animal room at a room temperature between 19 and 25° C. and humidity between 30 and 70% under illumination for 12 hours (from 7:00 a.m. to 7:00 p.m.) per day.

The rats were subjected to operation of partial urethral obstruction. Each rat was anesthetized by intraperitoneal administration of 50 mg/kg pentobarbital sodium (Dainippon Pharmaceutical Co., Ltd.) and placed in the supine position. The abdominal midline incision was made in a length of about 1 cm to expose the bladder, prostate and the urethra. After the bladder neck and base were peeled from the prostate, two surgical suture threads (No. 3, Natsume Seisakusho Co., Ltd.) were passed behind the urethral base. A polyethylene tube. (PE-200, Nippon Becton Dickinson Co., Ltd.) was placed along the urethra, and the urethra was loosely double-ligated together with the tube. The ligation was made in such a manner that the urethra was not pressed with the polyethylene tube and the suture was not slack. Then, the polyethylene tube was pulled out and the urethra was for partial urethral obstruction.

Subsequently, the rats were subjected to bladder indwelling catheterization. After the bladder was exposed, a polyethylene tube (PE-50, Nippon Becton Dickinson Co., Ltd.) was inserted from the bladder apex and fixed with a surgical suture. The other end of the tube was exposed subcutaneously from the back of the neck, plugged and then fixed to the skin with a surgical suture. The bladder was returned to its original position and the abdomen was sutured with a surgical thread.

Five to seven days after the operation of the partial urethral obstruction and the catheter implantation, the rats with partial urethral obstruction and the sham-operated rats were put in Bollman cages (KN-326-1, Natsume Seisakusho Co., Ltd.) under restraint. A three-way cock was connected to the bladder catheter. One end of the cock was connected to a pressure transducer (DX-360, Nihon Kohden Corp.), and the intravesical pressure signal was amplified via a strain pressure amplifier (AP-601G, Nihon Kohden Corp.), measured with a polygraph (RMP-6008, Nihon Kohden Corp.) and recorded on a thermal array recorder (RTA-1200, Nihon Kohden Corp.). The other end of the cock was connected to a syringe filled with a physiological saline (Otsuka Pharmaceutical Co., Ltd.) arranged to an infusion pump (KDS220, Neuro Science). An FD pick-up (TB-611T, Nihon Kohden Corp.) equipped with a cup was placed below the Bollman cage and connected to the strain pressure amplifier to record the micturition volume on a thermal array recorder as the change in tension. After the completion of the preparation for the measurement, a room temperature physiological saline was continuously infused into the bladder at a flow rate of 6 ml/h for about 30 minutes, and animals expressing regular micturition contractions were used in the test. After a stabilization period of 30 to 60 minutes, residual urine was manually expressed. Five minutes later, the intravesical saline infusion was started again, and the infusion was immediately stopped when micturition was observed. The bladder capacity was calculated from the period of time until occurrence of micturition (infusion rate 6 ml/h×infusion time). The residual urine volume was calculated by subtracting the micturition volume at the time of bladder contraction (voided volume per micturition) from the bladder capacity. Intravesical infusion of saline for 30 minutes was repeated twice to three times to measure the values before administration of a test compound or a vehicle. Then, the test compound or the vehicle (0.5 w/v% aqueous methylcellulose 400 cP solution) was orally administered. One, two and three hours after the administration, intravesical infusion of a physiological saline was carried out, and the bladder capacity, the micturition volume and the residual urine volume were measured. The average±standard error of the bladder capacity, the micturition volume and the residual urine volume was calculated for each group.

The results are shown as follows: Table 4, bladder capacity; Table 5, micturition volume; and Table 6, residual urine volume.

TABLE 4

| | Bladder capacity mL) | | | |
|---|---|---|---|---|
| | Before administration | After 1 hour | After 2 hours | After 3 hours |
| Control group | 0.42 ± 0.09 | 0.33 ± 0.09 | 0.28 ± 0.06 | 0.25 ± 0.06 |
| Compound 1 | 0.40 ± 0.04 | 0.54 ± 0.08 | 0.46 ± 0.07 | 0.44 ± 0.07 |

TABLE 5

| | Micturition volume (mL) | | | |
|---|---|---|---|---|
| | Before administration | After 1 hour | After 2 hours | After 3 hours |
| Control group | 0.29 ± 0.09 | 0.19 ± 0.08 | 0.15 ± 0.04 | 0.14 ± 0.03 |
| Compound 1 | 0.25 ± 0.04 | 0.36 ± 0.07 | 0.36 ± 0.07* | 0.27 ± 0.01** |

*$p < 0.05$,
**$p < 0.01$ (comparison with the control group) (n = 6-7; Student's t-test)

TABLE 6

| | Residual urine volume (mL) | | | |
|---|---|---|---|---|
| | Before administration | After 1 hour | After 2 hours | After 3 hours |
| Control group | 0.13 ± 0.05 | 0.14 ± 0.05 | 0.13 ± 0.03 | 0.11 ± 0.05 |
| Compound 1 | 0.15 ± 0.02 | 0.18 ± 0.07 | 0.10 ± 0.05 | 0.18 ± 0.07 |

According to the results of Test Example 2, Compound 1 tended to increase the bladder capacity and significantly increased the micturition volume. It was thus revealed that Compound 1 exhibits the activity to ameliorate the bladder irritative symptoms accompanied by partial urethral obstruction caused by benign prostatic hyperplasia, including the bladder hypertrophy.

Test Examples 1 and 2 show that Compound 1 has the activity to remit bladder irritative symptoms associated with benign prostatic hyperplasia, and Compound (I) is useful as a therapeutic agent for bladder irritative symptoms associated with benign prostatic hyperplasia.

TEST EXAMPLE 3

Acute Toxicity Test

The test compound was administered orally or intraperitoneally to animals per group of dd male mice (body weight: 20±1 g). The minimum lethal dose (MLD) value was obtained by observing mortality on the seventh day after the administration.

As a result, MLD of Compound 1 was >1000 mg/kg by orally administration administered.

Compounds (I) and pharmaceutically acceptable salts thereof can be used as such or in various pharmaceutical forms. The pharmaceutical compositions of the present invention can be produced by uniformly mixing an effective amount of Compound (I) or a pharmaceutically acceptable salt thereof, as an active ingredient, with a pharmaceutically acceptable carrier. It is preferable that these pharmaceutical compositions are in a unit dose form suitable for administration such as oral administration or parenteral administration (including intravenous administration).

In the preparation of compositions for oral administration, any useful pharmaceutically acceptable carriers can be used. For example, liquid preparations for oral administration such as suspensions and syrups can be produced using water, sugars such as sucrose, sorbitol and fructose, glycols such as polyethylene glycol and propylene glycol, oils such as sesame oil, olive oil and soybean oil, antiseptics such as p-hydroxybenzoates, flavors such as strawberry flavor and peppermint, or the like. Capsules, tablets, powders and granules can be produced using excipients such as lactose, glucose, sucrose and mannitol, disintegrators such as starch and sodium alginate, lubricants such as magnesium stearate and talc, binders such as polyvinyl alcohol, hydroxypropyl cellulose and gelatin, surfactants such as fatty acid esters, plasticizers such as glycerin, or the like. Tablets and capsules are the most useful unit dose forms for oral administration because of the easiness of administration. Solid pharmaceutical carriers are used for the production of tablets and capsules.

Injections can be prepared using, for example, carriers comprising distilled water, a salt solution, a glucose solution or a mixture of salt water and a glucose solution. They are prepared as solutions, suspensions or dispersed solutions using appropriate auxiliaries according to conventional methods.

Compounds (I) or pharmaceutically acceptable salts thereof can be administered orally in the above pharmaceutical forms or parenterally as an injection or the like. The effective dose and administration schedule vary depending upon the mode of administration, the age, body weight and condition of a patient, or the like, but they are usually administered in a dose of 1 to 900 mg/60 kg/day, preferably 1 to 200 mg/60 kg/day.

Certain embodiments of the present invention are illustrated in the following examples.

BEST MODES FOR CARRYING OUT THE INVENTION

Example 1

Tablets

Tablets having the following compositions were prepared according to a conventional method.

Compound 1 (250 g), mannitol (1598.5 g), sodium starch glycolate (100 g), light silicic acid anhydride (10 g), magnesium stearate (40 g) and yellow iron oxide (1.5 g) were mixed according to a conventional method. The resulting mixture was compressed using a tableting machine within 8 mm diameter punch and die (Purepress Correct-12, Kikusui Seisakusho Ltd.) to prepare tablets each containing 25 mg of the active ingredient.

The formulation is shown in Table 7.

TABLE 7

| Formulation | |
|---|---|
| Compound 1 | 25 mg |
| Mannitol | 159.85 mg |
| Sodium starch glycolate | 10 mg |
| Light silicic acid anhydride | 1 mg |
| Magnesium stearate | 4 mg |
| Yellow iron oxide | 0.15 mg |
| | 200 mg |

Example 2

Capsules

Capsules having the following composition were prepared according to a conventional method.

Compound 1 (500 g), lactose (300 g), light silicic acid anhydride (100 g) and sodium lauryl sulfate (100 g) were mixed according to a conventional method. The resulting mixture was encapsulated in hard capsules No. 1 (content: 100 mg/capsule) using a capsule filler (LZ-64, Zanasi) to prepare capsules each containing 50 mg of the active ingredient.

The formulation is shown in Table 8.

TABLE 8

| Formulation | |
|---|---|
| Compound 1 | 50 mg |
| Lactose | 30 mg |
| Light silicic acid anhydride | 10 mg |
| Sodium lauryl sulfate | 10 mg |
| | 100 mg |

Example 3

Injection

An injection having the following composition is prepared according to a conventional method.

Compound 1 (1 g) is dissolved in 100 g of purified soybean oil, and 12 g of purified egg yolk lecithin and 25 g of glycerin for injection are added thereto. The resulting mixture is made up to 1000 ml with distilled water for injection, kneaded and emulsified according to a conventional method. The obtained dispersed solution is aseptically filtered using a 0.2 μm disposable membrane filter and aseptically packed in glass vials in 2 ml portions to prepare an injection containing 2 mg of the active ingredient per vial.

The formulation is shown in Table 9.

TABLE 9

| Formulation | |
|---|---|
| Compound 1 | 2 mg |
| Purified soybean oil | 200 mg |
| Purified egg yolk lecithin | 24 mg |
| Glycerin for injection | 50 mg |
| Distilled water for injection | 1.72 ml |
| | 2.00 ml |

INDUSTRIAL APPLICABILITY

The present invention provides a therapeutic agent for bladder irritative symptoms associated with benign prostatic hyperplasia comprising, as an active ingredient, a tricyclic compound or a pharmaceutically acceptable salt thereof.

The invention claimed is:

1. A method for treating bladder irritative symptoms associated with benign prostatic hyperplasia, comprising administering to a patient suffering from bladder irritative symptoms associated with benign prostatic hyperplasia an effective amount of a tricyclic compound represented by formula (Ia):

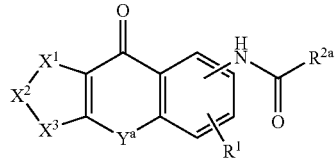

(Ia)

wherein
R$^1$ represents a hydrogen atom;
X$^1$-X$^2$-X$^3$ represents S—CR$^7$=CR$^8$ (wherein R$^7$ and R$^8$ represent hydrogen atoms);
Y$^a$ represents —CH$_2$SO$_2$—, and
R$^{2a}$ represents formula (II):

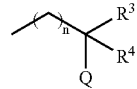

(II)

wherein n is 0; R$^3$ and R$^4$ independently represent a hydrogen atom, lower alkyl or trifluoromethyl; and Q represents hydroxy,
or a pharmaceutically acceptable salt thereof.

2. The method for treating bladder irritative symptoms associated with benign prostatic hyperplasia according to claim 1, wherein R$^3$ is methyl, R$^4$ is trifluoromethyl, and Q is hydroxy.

3. The method according to any of claim 1 or 2, wherein said bladder irritative symptoms are selected from the group consisting of urinary frequency, urinary urgency and reduced voided volume per micturition.

* * * * *

UNITED STATES PATENT AND TRADEMARK OFFICE
CERTIFICATE OF CORRECTION

PATENT NO. : 7,354,949 B2  
APPLICATION NO. : 10/472148  
DATED : April 8, 2008  
INVENTOR(S) : Tsuyoshi Yamagata et al.

Page 1 of 1

It is certified that error appears in the above-identified patent and that said Letters Patent is hereby corrected as shown below:

ON COVER PAGE AT (56) OTHER PUBLICATIONS

After "Yoshimura et al.": "Bladd r" should read --Bladder--.

ON COVER PAGE AT (57) ABSTRACT

Line 12, "13 $CH_2S$—," should read --$CH_2S$—,--.

COLUMN 2

Line 24, "$N(O)^m$" should read --$N(O)_m$--.

COLUMN 11

Line 63, "tube." should read --tube--.

COLUMN 12

Line 2, "was for partial urethral obstruction." should read --was partially obstructed.--; and  
Table 4, "mL)" should read --(mL)--.

COLUMN 16

Line 44, "any of" should be deleted.

Signed and Sealed this

Twelfth Day of August, 2008

JON W. DUDAS  
*Director of the United States Patent and Trademark Office*